(12) United States Patent
Venderpool et al.

(10) Patent No.: US 6,350,418 B1
(45) Date of Patent: Feb. 26, 2002

(54) LID LATCHING MECHANISM FOR STERILIZATION CONTAINER

(75) Inventors: Ronald L. Venderpool, Warsaw; Daniel Owens, Silver Lake, both of IN (US)

(73) Assignee: Paragon Group of Plastics Companies, Inc., Pierceton, IN (US)

( * ) Notice: Subject to any disclaimer, the term of this patent is extended or adjusted under 35 U.S.C. 154(b) by 0 days.

(21) Appl. No.: 09/251,275

(22) Filed: Feb. 16, 1999

Related U.S. Application Data (60) Provisional application No. 60/076,040, filed on Feb. 26, 1998.

(51) Int. Cl.⁷ .............................. A61L 2/00; E05C 1/06; B65D 83/10; B65D 25/00
(52) U.S. Cl. ...................... 422/297; 292/37; 206/363; 220/87.1; 220/315; 220/324
(58) Field of Search ................... 422/297, 300; 220/247, 243, 87.1, 315, 324, 325, 326; 206/438, 370, 363; 292/37

(56) References Cited

U.S. PATENT DOCUMENTS

| | | | |
|---|---|---|---|
| 654,044 A | * 7/1900 | Alexander | 292/37 |
| 1,534,341 A | * 4/1925 | Bernotow | 292/37 |
| 2,010,200 A | * 8/1935 | Rufener et al. | 292/37 |
| 2,473,065 A | * 6/1949 | Miller | 292/37 |
| 5,050,778 A | * 9/1991 | Corrado et al. | 222/152 |
| 5,281,400 A | * 1/1994 | Berry, Jr. | 422/295 |
| 5,407,648 A | 4/1995 | Allen et al. | |
| 5,441,707 A | 8/1995 | Lewis et al. | |
| 5,641,065 A | 6/1997 | Owens et al. | |
| 6,077,485 A | * 6/2000 | Baker | 422/300 |

* cited by examiner

Primary Examiner—Terrence R. Till
Assistant Examiner—Monzer R. Chorbaji
(74) Attorney, Agent, or Firm—Baker & Daniels (57) ABSTRACT

A sterilization container includes a base defining a volume for receiving medical instruments and a lid engaging the base and closing the top thereof. A latching mechanism mounted on the lid includes latching rods slidably mounted on the lid for engagement with apertures on the base to thereby secure the lid to the base. A camming member is rotatably mounted on the lid and includes slots engaged with the latching rods so that upon manual rotation of the camming plate in one direction the latching rods are moved into the apertures and upon rotation of the camming plate in the opposite direction, the latching rods are withdrawn from the apertures.

26 Claims, 6 Drawing Sheets

LID LATCHING MECHANISM FOR STERILIZATION CONTAINER

This application claims domestic priority under 35 USC 119(e) to provisional application 60/076,040, filed Feb. 26, 1998.

This invention relates to a mechanism for securing the lid of a sterilization container to the body of the container.

Medical instruments must be cleaned and sterilized before they are ready for reuse. Typical prior art sterilization containers are disclosed in U.S. Pat. Nos. 5,098,676; 5,407,648; and 5,441,707. Sterilization containers generally have an elongated body having bottom and side walls providing an open cavity which is closed by a removable lid during sterilization. It is desirable to be able to stack a number of such sterilization containers on top of one another and to be able to place several stacks of trays adjacent to one another for both storage and transport. Accordingly, it is desirable that the outer edges of the container be smooth and without protrusions or projecting components so that containers may be placed closely adjacent to one another, and it is also desirable that the lids of the sterilization containers be sufficiently flat that multiple containers may be stacked upon one another. Furthermore, it is desirable that the sterilization container includes a latching mechanism which secures the lid to the container during sterilization, but which permits the lid to be quickly and easily removed. The latching mechanism should secure all sides of the lid to the corresponding sides of the tray, but the latching mechanism should not extend beyond the edges of the tray for the reasons mentioned above. Some common prior art sterilization containers include latches on all four sides that require individual operation to latch and unlatch the lid, and which also project outwardly from the edges of the container and upwardly from the top of the container, thus making it difficult or impossible to stack trays upon one another and/or to arrange trays as closely adjacent to one another.

According to the present invention, a knob rotatably mounted in approximately the center of the lid rotates a camming member which simultaneously extends and retracts latching rods which are slidably supported on the lid and which extend into corresponding apertures on the sides of the tray when the lid is locked on the tray and are simultaneously retracted by the knob rotating the cam to permit the lid to be removed. The knob and a set of handles which permits the container to be lifted are recessed into the lid, thereby providing a flat upper surface so that the containers may be stacked upon one another.

These and other advantages of the present invention will become apparent from the following description, with reference to the accompanying drawings, in which:

Referring now to the drawings, a sterilization container generally indicated by the numeral 10 includes a base or tray 12 having opposite side walls 14, 16, opposite end walls 18, 20, and a bottom wall 22. The walls 14–22 define a container into which medical instruments are placed for sterilization. The open upper portion of the base 12 is closed by a lid 24. As illustrated in the drawings, the lid 24 is made of a transparent plastic, and the base or tray 12 is made from an opaque plastic. Openings 26 are provided in the bottom wall 22 to permit sterilization gases to enter the container. Apertures 28, 30 are provided in the end walls 18 and 20 respectively and are centered between the ends thereof, and are located just below the upper edges of the walls 18 and 20. Similarly, apertures 32, 34 are provided in the side walls 14, 16 at substantially the midpoint thereof and just below the upper edge thereof. Notches 36 are provided in the upper edge of the end wall 18, and notches 38 are provided in the upper edge of the end wall 20.

The lid 24 includes a perimetrically extending skirt generally indicated by the numeral 40 which extends around a substantially flat upper surface 42. The skirt 40 includes side edge portions 46, 44, which extend over the upper portions of the side edges 14, 16 when the lid is installed on the base or tray 12, and end edge portions 48, 50, which extend over the upper portion of the end edges 18, 20 when the lid 24 is installed on the base or tray 12.

Although the upper surface 42 of the top 24 is substantially flat, the surface 42 is provided with c-shaped recesses 52, 54, ends of which fit into the notches 36, 38 when the lid 24 is installed on the base or tray 12. The ends of wire handles 56, 58 are installed into appropriate openings provided on opposite sides of raised portions 60, 62 circumscribed by the grooves 52, 54. Each of the grooves 52, 54 are provided with upwardly curved portions 64, 66 which extend around latching rods 68, 70 to support the latter for movement toward and away from the end portions 48, 50 of the skirt 40 as will hereinafter be described. The rods 68, 70 also extend through similar curved raised portions 72, 74 provided within recesses in the raised portions 60, 62. The raised portions 72, 74 will be described in more detail hereinafter. The raised portions 64, 66 are lower than the upper surface 42, to permit the handles 56, 58 to be folded in a position such that they do not extend appreciably above the upper surface 42. The rods 68, 70 are aligned with the apertures 28, 30 so that the rods enter the apertures when the lid is latched to the body or tray 12, as will hereinafter be explained.

A second pair of latching rods 75, 78 are aligned with apertures 32, 34 in the side edges 14, 16 to engage the apertures 32, 34 when the lid 24 is latched to the base or tray portion 12. Rods 75, 78 are slidably mounted in raised rod supports 81, 83 defined within recesses 85, 87 adjacent the side edge portions 44, 46 of the skirt 40. Each of the latching rods 68, 70, 75, 78 has an end opposite the end engaging the corresponding aperture 28–34 that includes a downwardly projecting portion 76. Downwardly projecting portion 76 of rod 68 is engaged with a camming slot 79 on a circular camming plate 80, preferably made of stainless steel to withstand the effects of the sterilizing gases. The actuating rods are also preferably made of stainless steel. The downwardly extending portion 76 of actuating rod 75 extends into camming slot 82 of camming plate 80; the downwardly extending portion 76 of actuating rod 70 extends into the camming slot 84 of the camming plate 80; and the downwardly extending portion 76 of actuating rod 78 extends into camming slot 86 of camming plate 80. Semi-circular, Teflon coated, stainless steel washers 88 are welded or otherwise secured to the downwardly extending portion 76 of each of the rods 68, 70, 75, 78. The washers maintain the rods substantially horizontal and thereby prevent binding of the downwardly extending portions and their corresponding camming slots. The Teflon coating prevents metal-to-metal sliding contact, thereby facilitating smooth operation of the mechanism.

A substantially circular recess generally indicated by the numeral 90 is formed in substantially the center of the upper surface 42 of the lid 24. An aperture 92 substantially at the center of the circular recess 90 extends through the upper surface 42 of the lid 24. A screw and washer fastener 94 extends through an aperture 96 in the center of the camming plate 80 and then extends through the aperture 92 and is threadedly engaged with a manually operated plastic knob 98. Four arcuate slots 100 are formed concentrically with respect to circular recess 90, and each includes a pair of opposite ends 102, 104 defining a passage 106 therebetween. Each of the rods 68, 70, 75, 78 extend through a corresponding one of the passages 106 between adjacent arcuate slots 100. Each of the slots 79, 82, 84, and 86 of the camming plate 80 include an enlarged portion 108 with which the downwardly extending portions 76 of the actuating rods engage when the actuating rods are fully retracted.

In operation, the lid 24 is placed on the body or tray 12 after instruments to be sterilized have been placed in the body or tray 12. The knob 98 is then rotated in a clockwise direction, thereby permitting the camming slots 79, 82, 84 and 86 to drive their corresponding downwardly turned ends 76 and their corresponding actuating rods 68, 70, 75, 78 in a radially outwardly direction. Accordingly, as the downwardly turned ends 76 are driven radially outwardly, the actuating rods 68, 70, 75 and 78 are moved into the corresponding apertures 28, 30, 32 and 34 in the base or tray 12, thereby locking the lid 24 to the tray 12. When the lid is to be removed, knob 98 is rotated in a counterclockwise direction, thereby withdrawing the rods 68, 70, 75 and 78 from their apertures, permitting removal of the lid.

Figure 1:
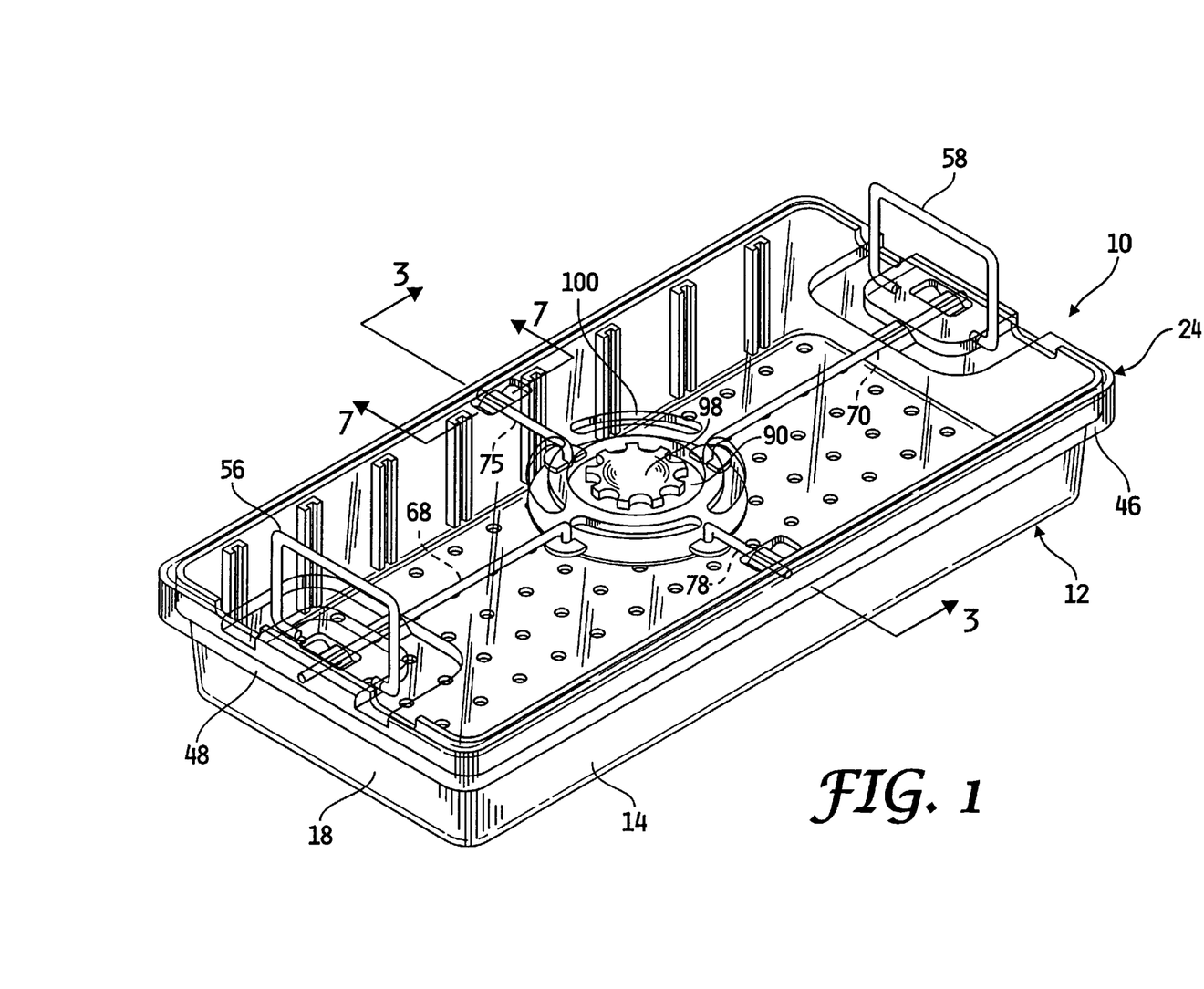
FIG. 1 is a view in perspective of a sterilization container made pursuant to the teachings of the present invention.
Figure 2:
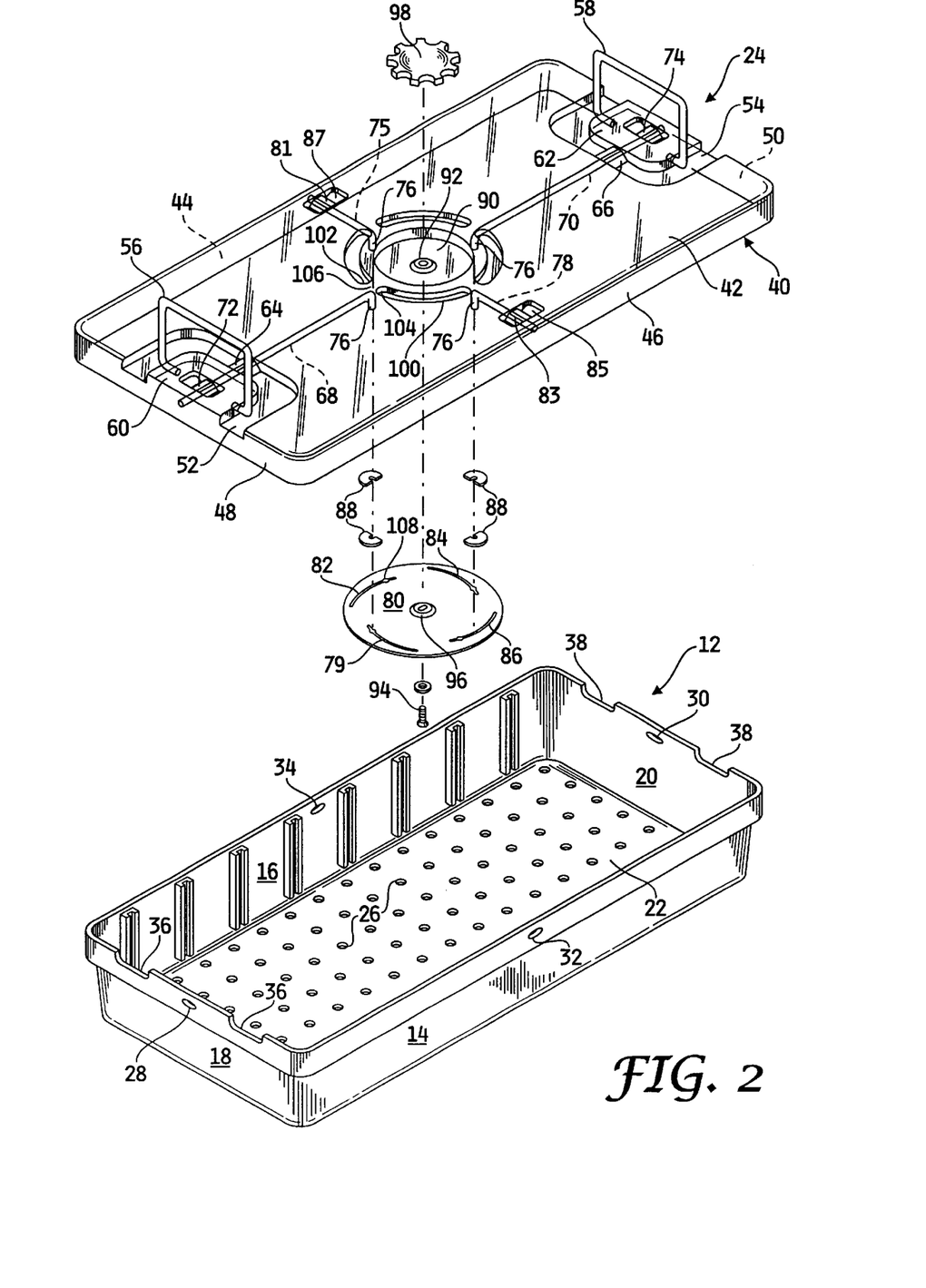
FIG. 2 is an exploded view in perspective of the sterilization container illustrated in FIG. 1.
Figure 3:
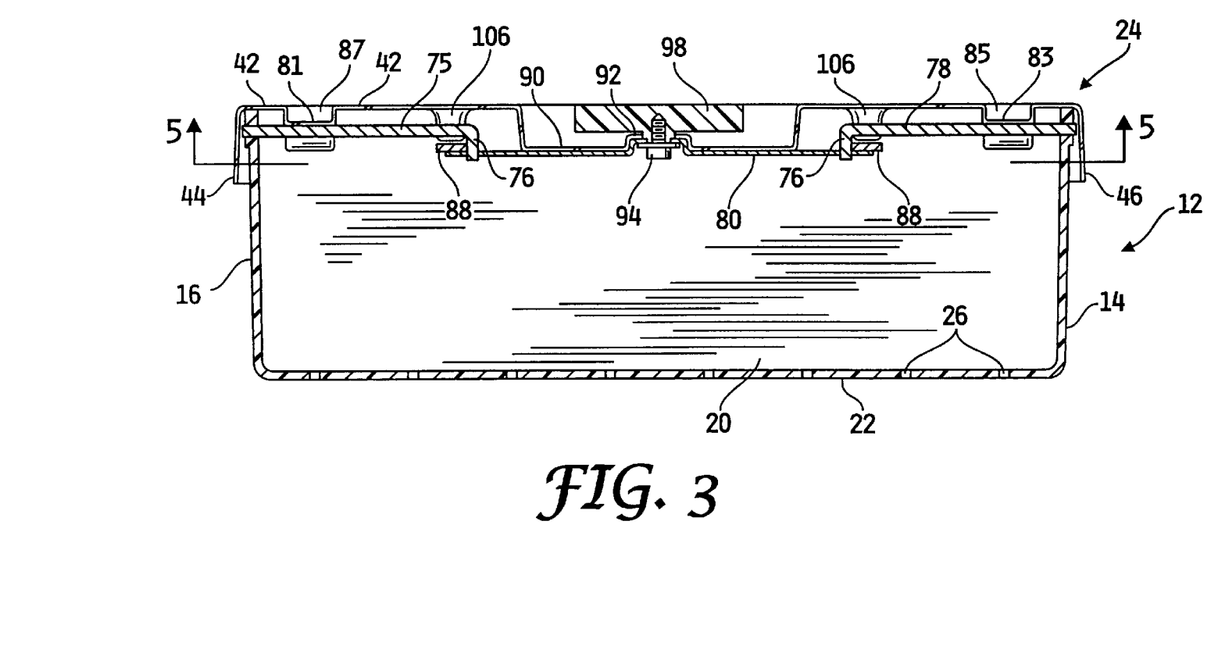
FIG. 3 is a cross-sectional view taken substantially along lines 3—3 of FIG. 1 and illustrating the lid secured to the body of the container.
Figure 4:
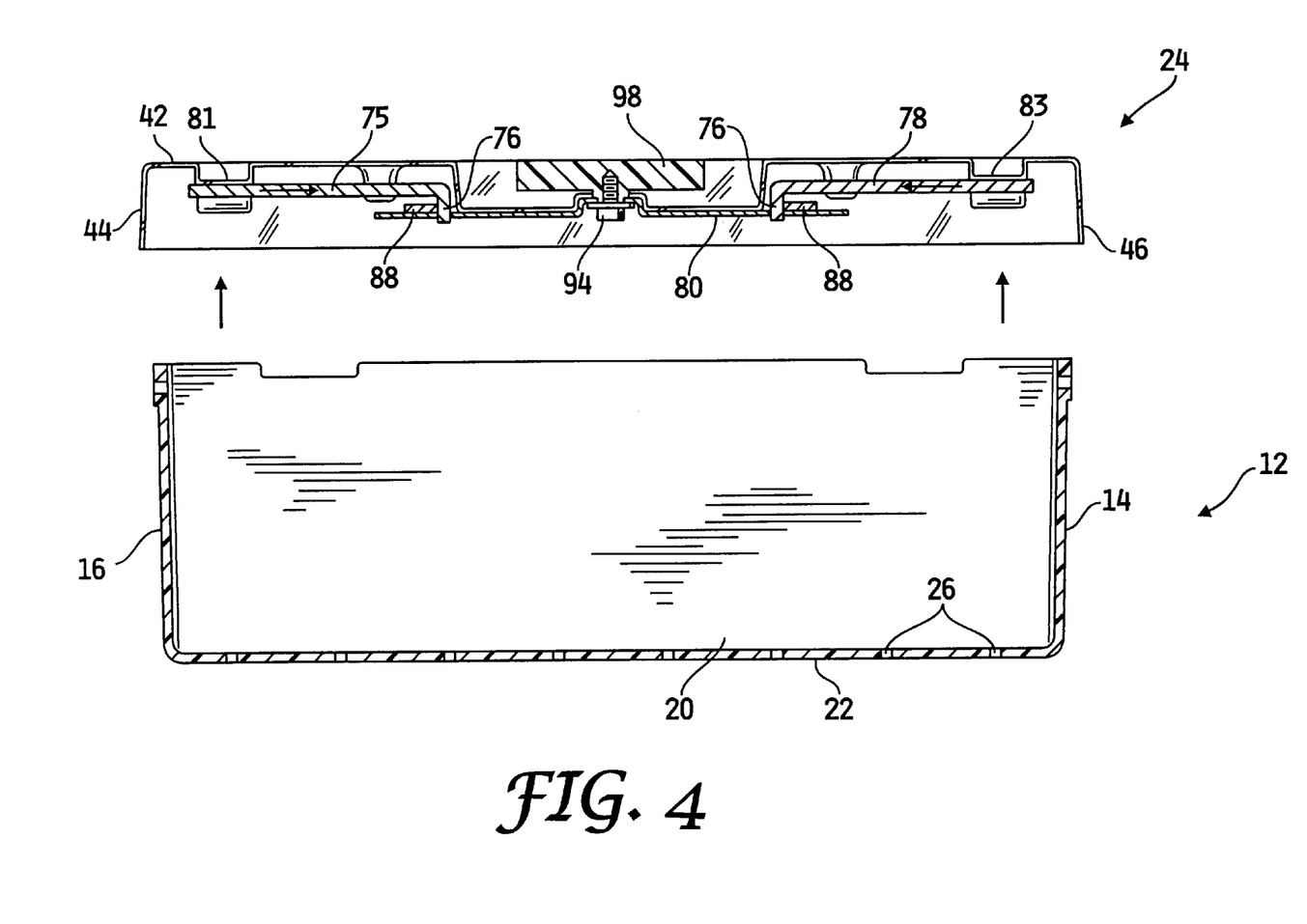
FIG. 4 is a cross-sectional view similar to FIG. 3, but illustrating the lid released and lifted off of the body of the sterilization container.
Figure 5:
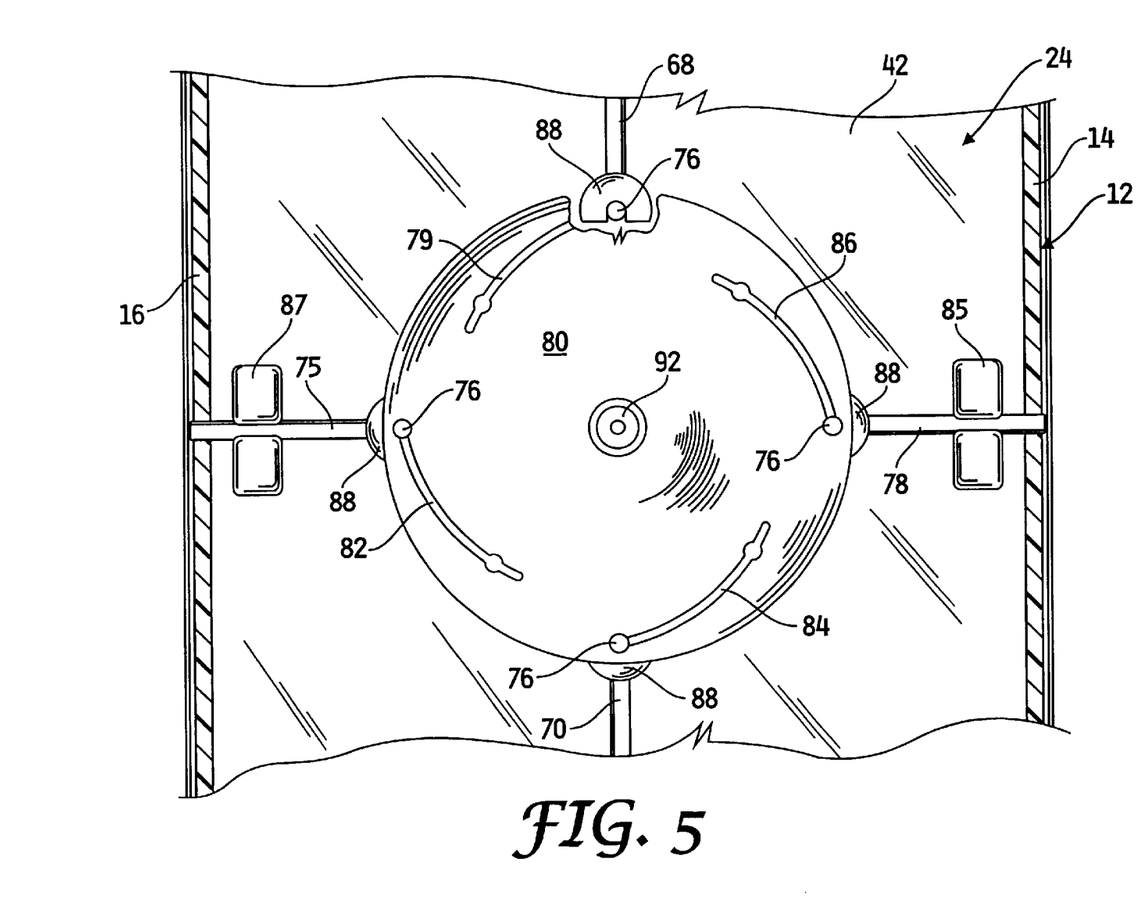
FIG. 5 is a view taken substantially along lines 5—5 of FIG. 3.
Figure 6:
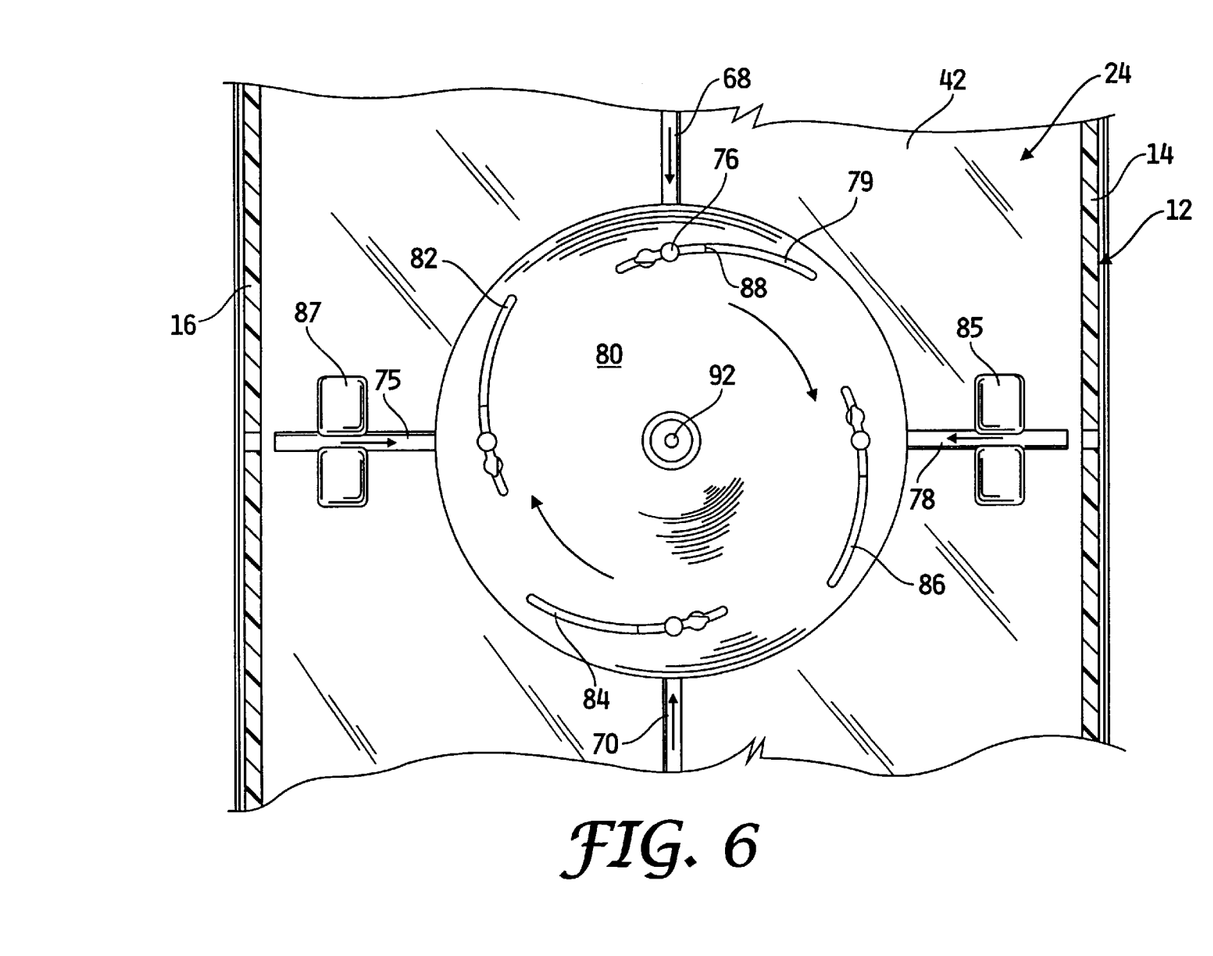
FIG. 6 is a view similar to FIG. 5, but illustrating the latches released to permit the lid to be lifted off of the body of the container.
Figure 7:
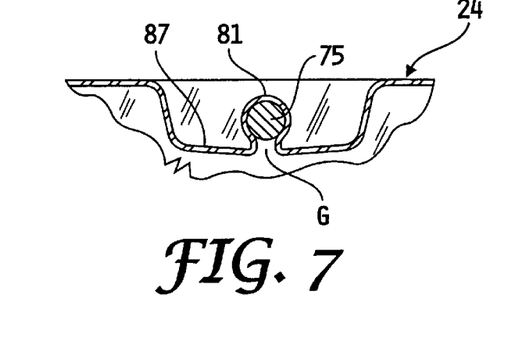
FIG. 7 is a fragmentary cross-sectional view taken substantially along lines 7—7 of FIG. 1.

Referring now to FIG. 7, which discloses in detail the recess 87 and raised portion 81 which is typical of the recesses supporting the outer ends of the rods 68, 70 and 78, the raised portion 81 substantially surrounds the actuating rod 75, leaving only a very small gap G. Accordingly, the raised portion 81 surrounds a sufficient portion of the rod 75 to support the rod from movement relative to the lid 24. The raised portion 81 is formed by use of a cylindrical silicon insert which is placed on a corresponding projecting portion of the mold from which the lid 24 is molded. The silicone plug is removed after molding is completed by using a rod to force the silicon inserts out of the raised portion 81.

What is claimed is:

1. Sterilization container comprising a base having side walls defining a volume and a lid engaging said side walls for closing said volume, and a latching mechanism movable between an actuated position for securing said lid on said side walls and a released position permitting the lid to be removed from the base, said latching mechanism including latching rods slidably mounted on said lid for movement toward and away from a corresponding one of said side walls, and a camming member rotatably mounted on said lid and engaged with said latching rods for moving the latter toward and away from their corresponding side wall.

2. Sterilization container as claimed in claim 1, wherein said camming member is a camming plate rotatably mounted on said lid, said camming plate having slots pivotably receiving a corresponding one of said latching rods.

3. Sterilization container as claimed in claim 2, wherein each of said side walls include apertures receiving a corresponding one of said latching rods when the latching rods are moved by said camming plate into a latched position in which the lid is secured to the base, said latching rods being withdrawn from said apertures when the latching rods are moved by said camming plate into a released position permitting said lid to be removed from said base.

4. Sterilization container as claimed in claim 3, wherein said camming plate is rotatable mounted for rotation about an axis at the center of said lid.

5. Sterilization container as claimed in claim 3, wherein said slots in said camming plate extend continuously between a radially innermost position and a radially outermost position, whereby rotation of the camming plate drives the latching rods outwardly with respect to the center of the camming plate when the camming plate is rotated in one direction and inwardly toward said axis when the camming plate is rotated in the opposite direction, to thereby engage said latching rods with their corresponding apertures when the camming plate is rotated in said one direction and to withdraw the camming plate is rotated in the opposite direction.

6. Sterilization container as claimed in claim 5, wherein said lid includes an inner surface facing into said volume when the lid is installed on the base and an opposite outer surface, said latching rods and said camming plate being supported on said inner surface.

7. Sterilization container as claimed in claim 3, wherein said lid includes a recess projecting into said volume when the lid is installed on the base, said camming plate being rotatably mounted on said inner surface of the recess via an axis extending through said lid, and a knob mounted on said axis and located within said recess whereby said outer surface is sufficiently flat that multiple ones of said containers may be stacked upon one another.

8. Sterilization container as claimed in claim 3, wherein said camming plate is rotatably mounted on one side of said lid via an axis extending through the lid, and a knob mounted on said axis on the other side of said lid for turning said plate.

9. Sterilization container as claimed in claim 3, wherein each of said latching rods terminate in a downwardly extending portion engaging a corresponding one of the apertures, and a support secured to the downwardly extending portion and slidably engaging said camming plate to support said latching rod off of said camming plate.

10. Sterilization container as claimed in claim 9, wherein said lid includes recesses extending into said volume, each of said latching rods extending through one of said recesses, said recesses including a circumscribing portion extending around a portion of said rod to sufficient to support said rod on said lid.

11. Sterilization container as claimed in claim 9, wherein said lid includes an inner surface facing into said volume when the lid is installed on the base and an opposite outer surface, said latching rods and said camming plate being supported on said inner surface.

12. Sterilization container as claimed in claim 3, wherein said lid includes recesses extending into said volume, each of said latching rods extending through one of said recesses, said recesses including a circumscribing portion extending around a portion of said rod to sufficient to support said rod on said lid.

13. Sterilization container comprising a base having side walls defining a volume and a lid engaging said side walls for closing said volume, and a latching mechanism movable between and actuated position for securing said lid on said side walls and a released position permitting the lid to be removed from the base, said latching mechanism including latching rods slidably mounted on said lid for movement toward and away from a corresponding one of said side walls, operating means for operating said latching rods, said lid including recesses extending into said volume, each of said latching rods extending through one of said recesses, said recesses including a circumscribing portion extending around a portion of said rod to sufficient to support said rod on said lid.

14. Sterilization container as claimed in claim 13, wherein said lid includes an inner surface facing into said volume when the lid is installed on the base and an opposite outer surface, said latching rods being supported on said inner surface.

15. A sterilization container comprising:
- a tray having a bottom wall, and side walls, which together define a volume, said side walls having a plurality of latching openings therethrough, adjacent to an upper edge of said sidewalls;
- a lid for enclosing said volume, said lid including lip portions extending over said side walls, and projecting downwardly over said latching openings;
- a latching mechanism attached to said lid and movable between an actuated position for securing said lid on said side walls and a released position permitting the lid to be removed from the base, said latching mechanism including latching rods slidably mounted on said lid for movement toward and away from a corresponding one of said side walls, and aligned with said plurality of openings, said latching rods being movable between positions extending through said openings and to positions retracted from said openings; and
- an actuation member mounted on said lid and engaged with said latching rods for moving the latter toward and away from their corresponding side wall.

16. The sterilization container of claim 15, wherein the actuation member is a rotary camming member.

17. The sterilization container of claim 16, wherein said camming member is a camming plate rotatably mounted on said lid, said camming plate having slots pivotably receiving a corresponding one of said latching rods.

18. The sterilization container of claim 17, wherein said camming plate is rotatable mounted for rotation about an axis at the center of said lid.

19. The sterilization container of claim 17, wherein said slots in said camming plate extend continuously between a radially innermost position and a radially outermost position, whereby rotation of the camming plate drives the latching rods outwardly with respect to the center of the camming plate when the camming plate is rotated in one direction and inwardly toward said axis when the camming plate is rotated in the opposite direction, to thereby engage said latching rods with their corresponding apertures when the camming plate is rotated in said one direction and to withdraw the camming plate is rotated in the opposite direction.

20. The sterilization container of claim 17, wherein said lid includes an inner surface facing into said volume when the lid is installed on the base and an opposite outer surface, said latching rods and said camming plate being supported on said inner surface.

21. The sterilization container of claim 17, wherein said lid includes a recess projecting into said volume when the lid is installed on the base, said camming plate being rotatably mounted on said inner surface of the recess via an axis extending through said lid, and a knob mounted on said axis and located within said recess whereby said outer surface is sufficiently flat that multiple ones of said containers may be stacked upon one another.

22. The sterilization container of claim 21, wherein said lid includes arcuate slots circumscribing said recess and extending into said volume, where adjacent slots form passages therebetween, each of said latching rods extending through one of said passages to said camming plate.

23. The sterilization container of claim 17, wherein said lid includes an inner surface facing into said volume when the lid is installed on the base and an opposite outer surface, said latching rods and said camming plate being supported on said inner surface.

24. The sterilization container of claim 15, wherein said camming plate is rotatably mounted on one side of said lid via an axis extending through the lid, and a knob mounted on said axis on the other side of said lid, and connected to said plate for turning said plate.

25. The sterilization container of claim 15, where each of said latching rods terminate in a downwardly extending portion engaging a corresponding one of the apertures, and a support secured to the downwardly extending portion and slidably engaging said camming plate to support said latching rod off of said camming plate.

26. The sterilization container of claim 15, wherein said lid includes recesses extending into said volume, each of said latching rods extending through one of said recesses, said recesses including a circumscribing portion extending around a portion of said rod to sufficient to support said rod on said lid.

* * * * *

UNITED STATES PATENT AND TRADEMARK OFFICE
CERTIFICATE OF CORRECTION

PATENT NO.    : 6,350,418 B1
DATED         : February 26, 2002
INVENTOR(S)   : Ronald L. Vanderpool and Daniel Owens It is certified that error appears in the above-identified patent and that said Letters Patent is hereby corrected as shown below:

<u>Title page,</u>
Inventor should be -- Ronald L. Vanderpool -- rather than "Ronald L. Venderpool"

<u>Column 4,</u>
Line 10, delete "rotatable" and insert -- rotatably --
Line 22, delete "is"
Line 52, delete "sufficient to" and insert -- sufficiently --
Line 63, delete "sufficient to" and insert -- sufficiently --

<u>Column 5,</u>
Line 1, delete "and" and insert -- an --
Line 10, delete "sufficient to" and insert -- sufficiently --
Line 46, delete "rotatable" and insert -- rotatably --

<u>Column 6,</u>
Line 48, delete "sufficient to" and insert -- sufficiently --

Signed and Sealed this

Twentieth Day of August, 2002

*Attest:*

JAMES E. ROGAN
*Attesting Officer*        *Director of the United States Patent and Trademark Office*